United States Patent
Fueyo et al.

(10) Patent No.: US 8,199,982 B2
(45) Date of Patent: *Jun. 12, 2012

(54) MAPPING OF LITERATURE ONTO REGIONS OF INTEREST ON NEUROLOGICAL IMAGES

(75) Inventors: Joanna Lynn Fueyo, Brighton, MA (US); Robert Lee Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

(*) Notice: Subject to any disclaimer, the term of this patent is extended or adjusted under 35 U.S.C. 154(b) by 900 days.

This patent is subject to a terminal disclaimer.

(21) Appl. No.: 12/141,316

(22) Filed: Jun. 18, 2008

(65) Prior Publication Data

US 2009/0316968 A1 Dec. 24, 2009

(51) Int. Cl.
*G06K 9/00* (2006.01)
(52) U.S. Cl. ............... 382/128; 382/132; 382/130
(58) Field of Classification Search .............. None
See application file for complete search history.

(56) References Cited

U.S. PATENT DOCUMENTS

| | | | |
|---|---|---|---|
| 5,832,450 A | 11/1998 | Myers et al. | |
| 5,845,255 A | 12/1998 | Mayaud | |
| 7,051,022 B1 | 5/2006 | Faisal | |
| 7,599,995 B1* | 10/2009 | Fernandez et al. | 709/206 |
| 2005/0038678 A1 | 2/2005 | Qian et al. | |
| 2005/0215889 A1 | 9/2005 | Patterson | |
| 2005/0244036 A1* | 11/2005 | Rusinek et al. | 382/120 |
| 2006/0120584 A1 | 6/2006 | Hillman | |
| 2007/0276777 A1 | 11/2007 | Krishnan et al. | |
| 2008/0077001 A1* | 3/2008 | Ruscio et al. | 600/407 |
| 2009/0006061 A1 | 1/2009 | Thukral et al. | |
| 2009/0124882 A1* | 5/2009 | Massie et al. | 600/407 |
| 2009/0149898 A1* | 6/2009 | Hulvershorn et al. | 607/3 |

FOREIGN PATENT DOCUMENTS

JP 2005-237441 A 9/2005

(Continued)

OTHER PUBLICATIONS

U.S. Appl. No. 12/169,339, filed Jul. 8, 2008, Fueyo et al.

(Continued)

*Primary Examiner* — Jermele M Hollington
*Assistant Examiner* — Trung Nguyen
(74) *Attorney, Agent, or Firm* — Yee & Associates, P.C.; John R. Pivnichny

(57) ABSTRACT

A computer implemented method, apparatus, and computer program product for analyzing neurological images. A set of brain scans for a patient is compared to a set of baseline control scans to automatically identify regions of interest in the set of patient scans. A region of interest is an area in a scan that shows an indication of a potential abnormality. A set of electronic medical literature sources is searched for medical literature relevant to the regions of interest in the set of patient scans. The relevant medical literature is correlated to the medical literature describing the regions of interest in the set of patient scans to the regions of interest in the set of patient scans. A result is generated. The result comprises the regions of interest and a set of links to the correlated portions of the relevant medical literature are outputted.

22 Claims, 4 Drawing Sheets

FOREIGN PATENT DOCUMENTS

JP      2006-204641 A      8/2006
WO    2007/063656 A1    6/2007

OTHER PUBLICATIONS

U.S. Appl. No. 12/169,402, filed Jul. 8, 2008, Fueyo et al.
U.S. Appl. No. 12/141,322, filed Jun. 18, 2008, Fueyo et al.
U.S. Appl. No. 12/169,329, filed Jul. 8, 2008, Fueyo et al.
U.S. Appl. No. 12/169,350, filed Jul. 8, 2008, Fueyo et al.
USPTO Notice of allowance for U.S. Appl. No. 12/169,402 dated Apr. 6, 2011.
USPTO office action for U.S. Appl. No. 12/169,402 dated Oct. 28, 2010.
USPTO Office action dated Jul. 7, 2011 for U.S. Appl. No. 12/141,322.

* cited by examiner

MAPPING OF LITERATURE ONTO REGIONS OF INTEREST ON NEUROLOGICAL IMAGES

BACKGROUND OF THE INVENTION

1. Field of the Invention

The present invention is related generally to a data processing system and in particular to a method and apparatus for managing neuropsychiatric disease data. More particularly, the present invention is directed to a computer implemented method, apparatus, and computer usable program code for automatically identifying regions of interest in brain scans and mapping relevant portions of medical literature to those regions of interest.

2. Description of the Related Art

Neuropsychiatric disorders are disorders that have neurological features associated with disorders of the nervous system, as well as psychiatric features. Neuropsychiatric disorders may be treated using a variety of therapies, such as talk therapy, behavioral therapy, chemical therapy, and/or mechanical therapy. Chemical therapy refers to pharmacotherapy, such as, the utilization of drugs. Mechanical therapy includes electroconvulsive therapies (ECT). These therapies may be used separately or may be used in combination to treat patients diagnosed with neuropsychiatric disorders.

However, many of these patients may not receive the most effective treatments due to difficulties in accurately diagnosing patients with neuropsychiatric disorders. Patients that are accurately diagnosed may also suffer from the side effects of both effective therapies and trails of ineffective therapies. Furthermore, some patients may suffer for years as a result of poorly understood disease phenotype, particularly in cases involving the presentation of complex cases. In addition, when a disease is developing in a patient and the patient has not had a sufficient number of "episodes" for diagnosis or has only manifested a few early stage symptoms, it may be difficult or impossible to clearly and rapidly delineate a differential diagnosis.

BRIEF SUMMARY OF THE INVENTION

According to one embodiment of the present invention, a computer implemented method, apparatus, and computer program product for analyzing neurological images is provided. A neuroimage mapping manager compares a set of brain scans for a patient to a set of baseline control scans to automatically identify a set of regions of interest in the set of patient scans. The set of brain scans for the patient may include a set of positron emission tomography scans of the patient and/or a set of magnetic resonance imaging scans of the patient. A region of interest is an area in a scan that shows an indication of a potential abnormality. The neuroimage mapping manager searches a set of electronic medical literature sources for medical literature relevant to the regions of interest in the set of patient scans to form relevant medical literature.

The neuroimage mapping manager correlates portions of the relevant medical literature describing the set of regions of interest in the set of patient scans to the set of regions of interest in the set of patient scans to form correlated portions of the relevant medical literature. The portions of the relevant medical literature describing the set of regions of interest in the set of patient scans comprises a set of brain scans in the relevant medical literature showing areas of a brain having an identified abnormality that corresponds to the potential abnormality shown in the set of regions of interest in the set of patient scans. The neuroimage mapping manager then generates a result. The result comprises the set of patient scans and a set of links to the correlated portions of the relevant medical literature.

In one embodiment, the neuroimage mapping manager presents the set of regions of interest to a user. In response to receiving a selection of a set of additional regions of interest in the set of patient scans from the user to form a set of user selected regions of interest, the neuroimage mapping manager adds the set of user selected regions of interest to the set of regions of interest in the patient scans. The neuroimage mapping manager automatically removes unselected regions from the set of regions of interest.

In another embodiment, searching the set of electronic medical literature sources further comprises identifying the set of electronic medical literature sources; and searching medical literature available from the set of electronic medical literature sources using at least one of data mining, pattern recognition, search engines, queries to identify the relevant medical literature in the medical literature available from the set of electronic medical literature sources, data mining cohort, pattern recognition cohort, search engine cohort, or any other cohort appliance of interest. A cohort is a group of one or more objects having a common characteristic. For example, a data mining cohort may be, without limitation, a group of one or more objects associated with performing data mining techniques to identify desired data from a data source. A pattern recognition cohort may be, without limitation, a group of pattern recognition software applications that identify patterns in data, such as medical data.

The set of baseline control scans comprises a set of baseline normal scans and/or a set of baseline abnormal scans. In response to receiving a set of brain scans for a set of healthy subjects in various demographic groups to form the baseline normal scans, the neuroimage mapping manager analyzes the baseline normal scans to identify a normal appearance of areas in normal brain scans, wherein a normal brain scan is a scan that does not show indications of disease or abnormalities in the areas in the normal brain scans. In response to receiving a set of brain scans for a set of subjects in various demographic groups having identified abnormalities in the set of brain scans to form the baseline abnormal scans, the neuroimage mapping manager analyzes the baseline abnormal scans to identify an abnormal appearance of areas in brain scans, wherein an abnormal scan is a scan that shows indications of disease or abnormalities in the areas of the brain scans.

DETAILED DESCRIPTION OF THE INVENTION

Figure 1:
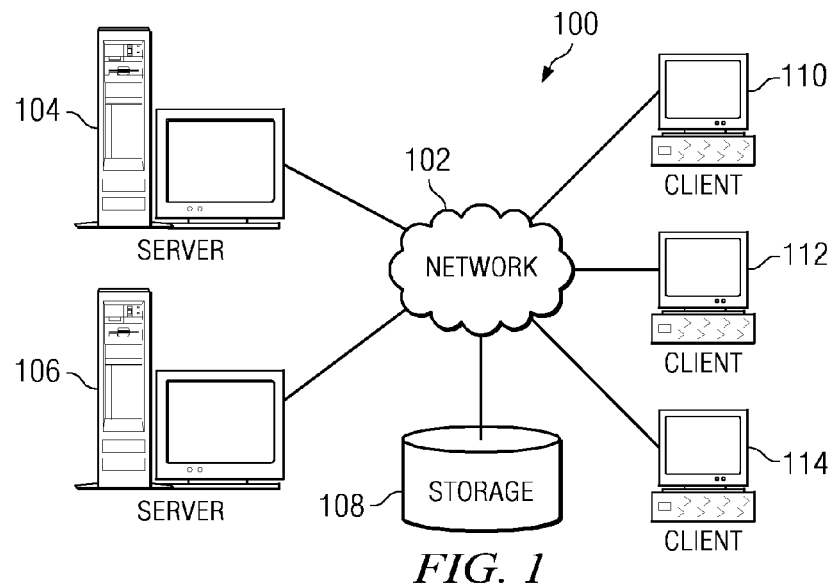
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
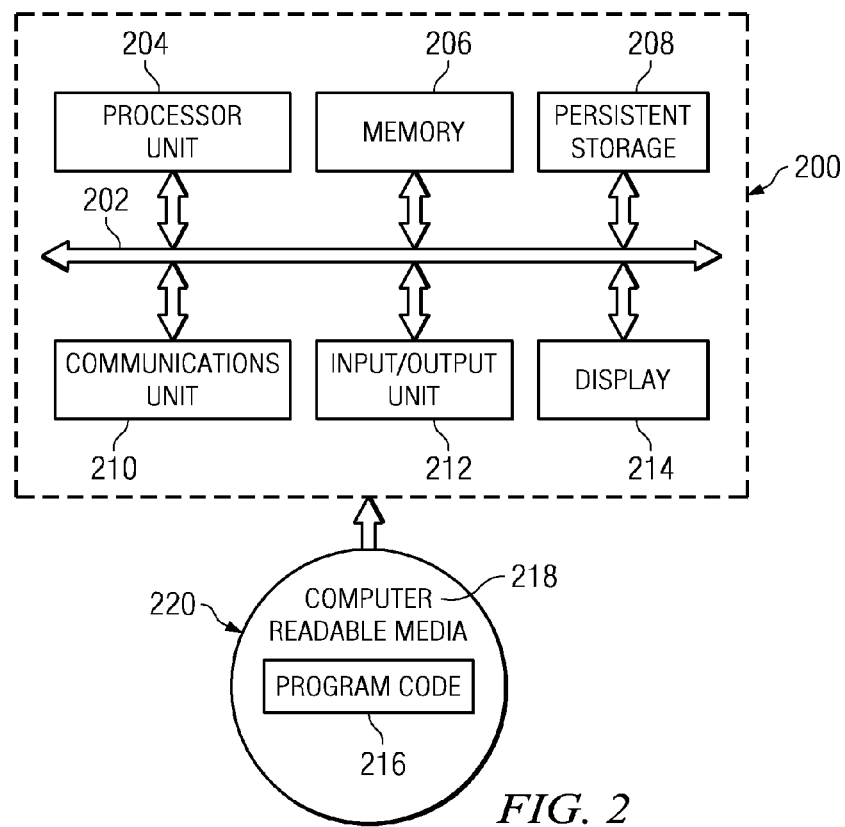
FIG. 2 is a block diagram of a data processing system in which illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments recognize that some patients may suffer from the ineffective remediation and/or treatment of neuropsychiatric conditions using pharmaceuticals, as well as side effects of both effective and ineffective therapies. Furthermore, many patients suffer for years as a result of poorly understood disease phenotype, particularly in presentation of neuropsychiatric conditions that may not be completely understood by the medical community. A neuropsychiatric condition is a condition that involves neurological and/or psychiatric features, such as, without limitation, depression, schizophrenia, bipolar disorder, and any other neuropsychiatric disorders.

Therefore, according to one embodiment of the present invention, a computer implemented method, apparatus, and computer program product for analyzing neurological images is provided. A neuroimage mapping manager compares a set of brain scans for a patient to a set of baseline control scans to automatically identify set of regions of interest in the set of patient scans. The term "set" refers to one or more. The set of brain scans may include a single brain scan, as well as two or more brain scans. The set of brain scans for the patient may include a set of positron emission tomography scans of the patient and/or a set of magnetic resonance imaging scans of the patient. A region of interest is an area in a scan that shows an indication of a potential abnormality. The potential abnormality may include, without limitation, abnormal functionality, abnormal brain structure, a disease, an illness, brain damage, abnormal brain metabolism, or any other abnormality. The neuroimage mapping manager searches a set of electronic medical literature sources for medical literature relevant to the set of regions of interest in the set of patient scans to form relevant medical literature.

The neuroimage mapping manager correlates portions of the relevant medical literature describing the set of regions of interest in the set of patient scans to the set of regions of interest in the set of patient scans to form correlated portions of the relevant medical literature. The portions of the relevant medical literature describing the set of regions of interest in the set of patient scans comprises a set of brain scans in the relevant medical literature showing areas of a brain having an identified abnormality that corresponds to the potential abnormality shown in the set of regions of interest in the set of patient scans. The neuroimage mapping manager then generates a result. The result comprises the set of patient scans and a set of links to the correlated portions of the relevant medical literature.

In one embodiment, the neuroimage mapping manager presents the set of regions of interest to a user. The regions of interest may be presented in a visual format, an audio format, a combination of audio and visual format, or any other format. In response to receiving a selection of an additional region of interest in the set of patient scans from the user to form a user selected region of interest, the neuroimage mapping manager adds the user selected region of interest to the regions of interest in the patient scans.

In another embodiment, searching the set of electronic medical literature sources further comprises identifying the set of electronic medical literature sources; and searching medical literature available from the set of electronic medical literature sources using at least one of data mining, search engines, and queries to identify the relevant medical literature in the medical literature available from the set of electronic medical literature sources.

The set of baseline control scans comprises a set of baseline normal scans and/or a set of baseline abnormal scans. In response to receiving a set of brain scans for a set of healthy subjects in various demographic groups to form the baseline normal scans, the neuroimage mapping manager analyzes the baseline normal scans to identify a normal appearance of areas in normal brain scans, wherein a normal brain scan is a scan that does not show indications of disease or abnormalities in the areas in the normal brain scans. In response to receiving a set of brain scans for a set of subjects in various demographic groups having identified abnormalities in the set of brain scans to form the baseline abnormal scans, the neuroimage mapping manager analyzes the baseline abnormal scans to identify an abnormal appearance of areas in brain scans, wherein an abnormal scan is a scan that shows indications of disease or abnormalities in the areas of the brain scans.

Figure 3:
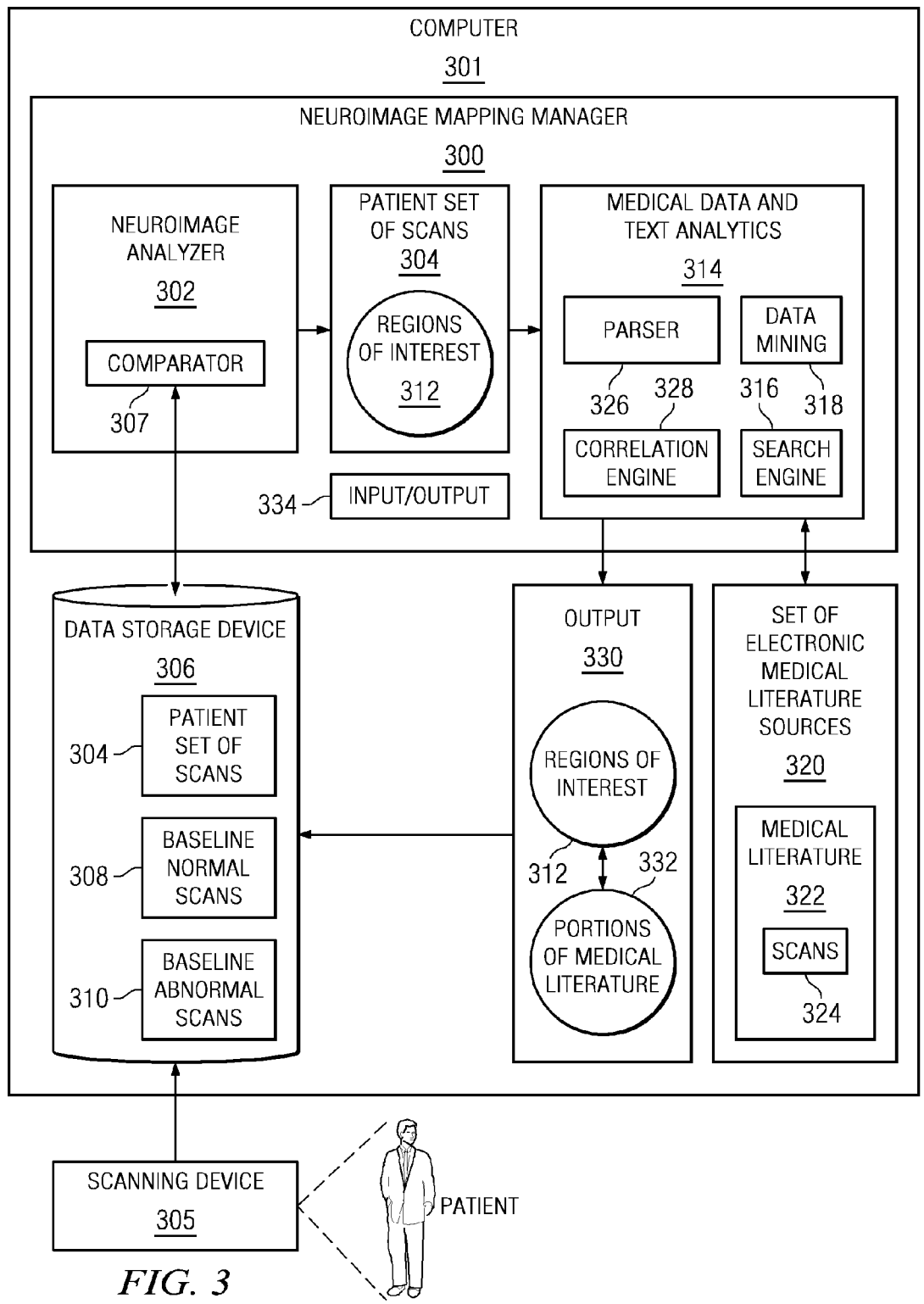
FIG. 3 is a block diagram of a neuroimage mapping manager in accordance with an illustrative embodiment.

FIG. 3 is a block diagram of a neuroimage mapping manager in accordance with an illustrative embodiment. Neuroimage mapping manager 300 is software for analyzing patient brain scans to identify regions of interest in the brain scans and generate links to portions of interest in the medical literature. Computer 301 may be implemented in any type of computing device, such as, without limitation, a server, a client, a laptop computer, a personal digital assistant (PDA), a smart phone, or any other known or available computing device.

Neuroimage analyzer 302 receives patient set of scans 304. Patient set of scans 304 is a set of one or more brain scans. Patient set of scans 304 may include functional magnetic resonance imaging (FMRI) scans, structural magnetic resonance imaging (sMRI) scans, positron emission tomography (PET) scans, or any other type of brain scans.

The scans in patient set of scans are generated by scanning device 305. Scanning device 305 may be implemented as a functional magnetic resonance imaging device, a structural magnetic resonance imaging device, a positron emission tomography device, or any other type of device for generating scans of a patient's brain. Scanning device 305 saves the scans of the patient's brain in data storage device 306 as patient set of scans 304.

Data storage device 306 may be implemented as a hard drive, a flash memory, a main memory, read only memory (ROM), a random access memory (RAM), or any other type of data storage device. Data storage may be implemented in a single data storage device or a plurality of data storage devices. Data storage device 306 may be local to computer 301 or remote to computer 301.

Neuroimage analyzer 302 may receive the scans in patient set of scans 304 from scanning device 305 as each scan is generated or neuroimage analyzer 302 may retrieve the scans from a pre-generated set of scans, such as patient set of scans 304 in data storage device 306. Neuroimage analyzer 302 analyzes patient set of scans 304 to identify regions of interest in the scans based on baseline normal scans and/or baseline abnormal scans for identified illnesses, abnormalities, diseases, or disorders.

A region of interest is an area in a scan that shows an indication of a potential abnormality, a potential illness, a potential disease, a potential problem with metabolism, or any other deviation from what would be expected in a scan of the region for a healthy individual having similar characteristics as the patient. The similar characteristics may include, without limitation, an age range of the patient, race, gender, or other factors influencing the development and appearance of regions of the brain in a scan.

Comparator 307 is a software component that compares patient set of scans 304 to baseline normal scans 308 and/or baseline abnormal scans 310. A baseline normal scans 308 is a set of one or more brain scans for average, healthy subjects having one or more characteristics in common with the patient. The characteristics in common may be any common characteristic, such as, without limitation, age, gender, race, pre-existing conditions, profession, place of residence, nationality, or any other characteristic. For example, if the patient is a sixteen year old female, baseline normal scans 308 may include scans of normal, healthy female subjects between the ages of fourteen and eighteen.

Comparator 307 compares one or more areas in each scan in patient set of scans 304 with corresponding areas in one or more scans in baseline normal scans 308 to identify areas of the patients scans that are consistent with the scans of normal, healthy subjects and to identify areas of the scans that are inconsistent with the scans of normal, healthy subjects. An area in a scan that is inconsistent with the corresponding areas in baseline normal scans 308 are identified as regions of interest 312. A region identified in regions of interest 312 may indicate a potential abnormality, illness, or condition. However, the regions in regions of interest 312 are not required to definitively indicate an abnormality, illness, condition, or other deviation from the norm.

Baseline abnormal scans 310 is a set of one or more scans of subjects having one or more characteristics in common with the patient and diagnosed with an identified condition. The identified condition may be a disease, an illness, a deformity, an abnormality, or any other identified deviation from the norm. For example, if the patient is a male, age thirty five, and diagnosed with diabetes, the baseline abnormal scans may include scans of male patients between the ages of thirty and forty and having a variety of known neuropsychiatric disorders. Comparator 307 compares regions in each scan in patient set of scans 304 with one or more scans in baseline abnormal scans 310 to identify regions of interest in the patient's scans that show indications of neuropsychiatric disorders, illness, disease, or abnormalities. A region in a scan may show indications of a potential illness, condition, abnormality, or neuropsychiatric disorder if the region in the patient's scan is consistent with a corresponding region in a brain scan of a subject having a known illness, condition, abnormality, or neuropsychiatric disorder.

Medical data and text analytics 314 is a software component for searching a set of electronic medical literature sources for medical literature relevant to regions of interest 312 in patient set of scans 304 and correlate portions of the relevant medical literature describing the regions of interest in the set of patient scans to regions of interest 312.

Search engine 316 is any type of known or available information retrieval software for locating medical literature that is relevant to regions of interest 312 in one or more sources. Search engine 316 may be software for searching data storage devices on a computer system or a web search tool for searching for medical information on the World Wide Web. Search engine 316 may also make queries into databases, information systems, and other medical literature information sources to locate information relevant to regions of interest 312. Data mining 318 is a software tool for searching through information available from one or more sources and retrieving medical information relevant to regions of interest 312.

Data mining 318, search engine 316, or any other software for locating relevant information may be used to search set of electronic medical literature sources 320 for relevant medical literature. Set of electronic medical literature sources 320 may include both online medical literature sources that are accessed by computer 301 via a network connection, as well as off-line medical literature sources that may be accessed without a network connection. An example of an electronic medical literature source includes, without limitation, PUBMED. Medical literature 322 is any literature, journal article, medical study results, medical text, pharmaceutical studies, or any other medical information in an electronic format. Medical literature 322 may include scans 324, such as magnetic resonance imaging scans, positron emission tomography scans, or any other type of brain scans.

Parser 326 is software for parsing medical literature 322 text into a form suitable for further analysis and processing. Parser 326 may be implemented as any type of known or available parser. Correlation engine 328 correlates portions of medical literature 332 with regions of interest 312. A portion of medical literature is a section of medical literature text and/or one or more scans that describe a region of interest, describe a condition, illness, deformity, abnormality, disease, or other cause for an appearance of a region of interest, an area in a scan that is the same or similar to an area of interest, or otherwise is associated with a region of interest.

Neuroimage mapping manager 300 generates output 330, including regions of interest 312 and portions of medical literature 332. Regions of interest 312 may be output with a set of links to portions of medical literature 332 embedded in set of scans 304 or embedded within regions of interest 312. In another embodiment, links to portions of medical literature 332 may be output as results that are separate from patient set of scans 304. In another embodiment, the set of links to portions of medical literature 332 are embedded in an electronic medical file for the patient. A user selects a link in the set of links to view a portion of medical literature associated with a region of interest. The portion of medical literature may be a scan only, text only, or a combination of text and one or more scans. The portion of medical literature may be an entire or complete item, such as a complete medical journal article or a complete section of a medical textbook. The portion of medical literature may also be a portion of a journal article, a portion of a section of a medical textbook, or other part of an item of medical literature.

In this embodiment, baseline normal scans 308 and baseline abnormal scans 310 are pre-generated and available for retrieval from data storage device 306. However, in another embodiment, medical data and text analytics 314 searches set of electronic medical literature sources 320 for scans of normal, healthy subjects to create baseline normal scans 308. Medical data and text analytics 314 also searches set of electronic medical literature sources 320 for scans of subjects having known abnormalities, deformities, illnesses, ailments, diseases, or other neuropsychiatric disorders to create baseline abnormal scans 310.

Thus, neuroimage mapping manager 300 provides data and text analytics to automatically determine regions of a patient's brain affected by disease as depicted in functional neuroimage data, such as functional magnetic resonance imaging scans and positron emission tomography scans. Neuroimage mapping manager 300 applies technologies to data, such as heuristics, which automatically correlate the affected brain region with portions of medical literature 322 that describes the regions of interest 312 found in both functional and structural data in patient set of scans 304.

Input/output 334 may be implemented as any type of input and/or output device for presenting regions of interest 312 to a user and/or receiving a selection of one or more regions of interest in patient set of scans 304 from a user. In other words, neuroimage analyzer 302 automatically identifies one or more regions of interest in patient set of scans 304. Neuroimage analyzer 302 may optionally present the automatically selected regions of interest to the user using input/output 334.

The automatically selected regions of interest may be presented using a display device to present the regions of interest in a visual format, using an audio device to present the regions of interest to the user in an audio format, using a combination of audio and visual devices, or any other presentation device. The user may choose to select one or more additional regions of interest in patient set of scans 304. In such a case, neuroimage analyzer 302 adds the manually selected set of one or more regions of interest to regions of interest 312. In another embodiment, the user may choose to de-select or remove one or more regions of interest from the automatically selected regions of interest. In such a case, neuroimage analyzer 302 automatically removes the one or more regions of interest selected for removal by the user from regions of interest 312.

Figure 4:
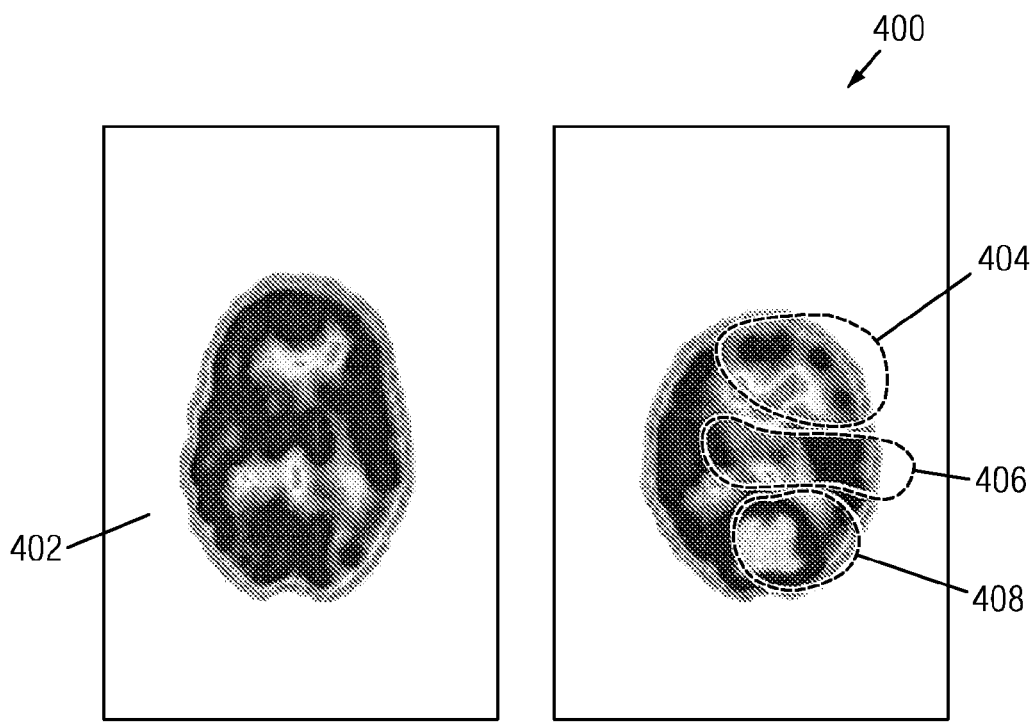
FIG. 4 is a block diagram of a magnetic resonance imaging brain scan having regions of interest in accordance with an illustrative embodiment.

Referring to FIG. 4, a block diagram of a magnetic resonance imaging brain scan having regions of interest is depicted in accordance with an illustrative embodiment. Scan 400 is a positron emission tomography scan of a brain of a patient. Scan 402 is a positron emission tomography scan of a normal, healthy subject. Scan 400 has regions of interest 404-408. Regions of interest 404-408 are areas in scan 400 that show indications of schizophrenia or any other abnormality. In this example, regions of interest 404-408 show disruptions in brain activity. Region 406 shows abnormal changes in the ventricles of the brain. Region 408 shows decreased function in the frontal section.

Figure 5:
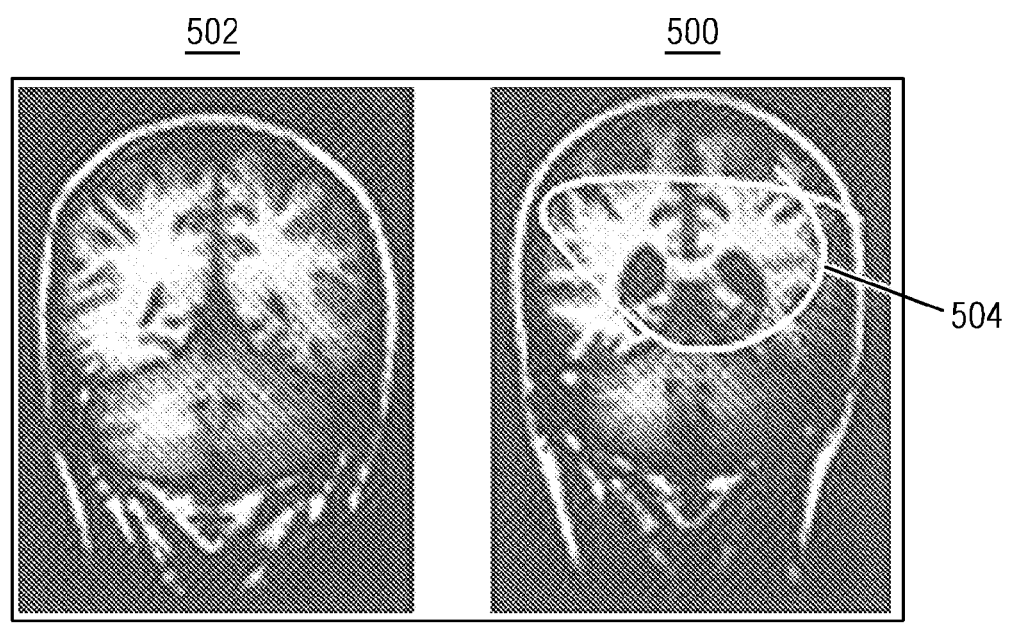
FIG. 5 is a positron emissions tomography brain scan having regions of interest in accordance with an illustrative embodiment.

Turning now to FIG. 5, a positron emissions tomography brain scan having regions of interest is shown in accordance with an illustrative embodiment. Scan 500 is a magnetic resonance imaging scan of a patient's brain. Scan 502 is a magnetic resonance imaging scan of a normal, healthy subject's brain. Scan 500 includes region of interest 504. Region 504 shows an abnormal enlargement of the ventricles of the brain when compared with scan 502 of a normal, healthy subject. The enlargement of the ventricles shown in region of interest 504 may indicate an illness or disease, such as, without limitation, schizophrenia. Therefore, a neuroimage mapping manager identifies region 504 as a region of interest.

Figure 6:
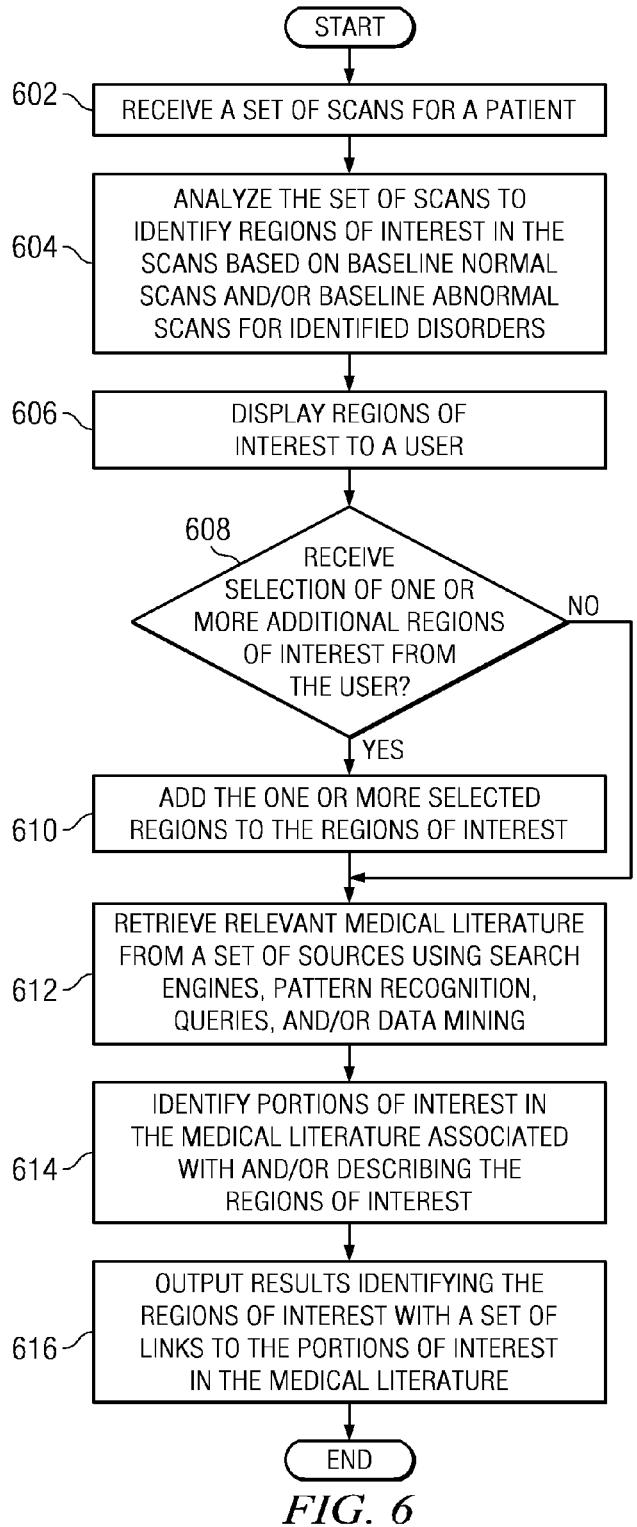
FIG. 6 is a flowchart illustrating a process for analyzing a set of brain scans for a patient to identify regions of interest with links to relevant portions of the medical literature in accordance with an illustrative embodiment.

FIG. 6 is a flowchart illustrating a process for analyzing a set of brain scans for a patient to identify regions of interest with links to relevant portions of the medical literature in accordance with an illustrative embodiment. The process in FIG. 6 may be implemented by software for analyzing patient brain scans to identify regions of interest in the brain scans and generate links to portions of interest in the medical literature, such as neuroimage mapping manager 300 in FIG. 3.

The neuroimage mapping manager receives a set of scans for a patient (step 602). The set of scans may include functional magnetic resonance imaging (fMRI) scans, structural magnetic resonance imaging (sMRI) scans, positron emission tomography (PET) scans, or any other type of brain scans. The neuroimage mapping manager analyzes the set of scans to identify regions of interest in the scans based on baseline normal scans and/or baseline abnormal scans for identified disorders (step 604). The neuroimage mapping manager displays the identified regions of interest to a user (step 606). The neuroimage mapping manager makes a determination as to whether a selection of one or more additional regions of interest is received from the user (step 608).

If a selection of one or more additional regions of interest is received from the user, the neuroimage mapping manager adds the one or more selected regions to the regions of interest (step 610). After adding the selected regions to the regions of interest at step 610 or if no selections of additional regions are received from the user at step 608, the neuroimage mapping manager retrieves relevant medical literature from a set of sources using search engines, pattern recognition, queries, and/or data mining (step 612). The embodiments are not limited to using only search engines, queries, and data mining. Any known or available method for locating desired information in an electronic data source may be utilized.

Next, the neuroimage mapping manager identifies portions of interest in the medical literature associated with and/or describing the regions of interest (step 614). The portions of interest may include pages, paragraphs, or portions of text describing one or more of the regions of interest, the appearance of one or more of the regions of interest, or the characteristics of one or more of the regions of interest. The portions of interest in the relevant medical literature may include images of scans containing one or more of the regions of interest, portions of text in the medical literature describing diseases, deficiencies, illnesses, and/or abnormalities that may cause the appearance of one or more of the regions of interest or one or more characteristics of the regions of interest, or any other portion of medical literature that is relevant to one or more of the regions of interest in the patient's scans.

The neuroimage mapping manager outputs results identifying the regions of interest with a set of links to the portions of interest in the medical literature (step 616) with the process terminating thereafter.

In this embodiment, the regions of interest are displayed to the user and the user is given an opportunity to select one or more additional regions of interest to add to the regions of interest identified by the neuroimage mapping manager. In another embodiment, the regions of interest are not presented to the user prior to identifying the portions of interest in the medical literature. In this embodiment, the user is not required to review the regions of interest and provide input as to whether to add one or more additional regions of interest. In this case, the process may occur completely automatically without any user input during the process of analyzing the patient's scans to identify regions of interest and linking portions of the relevant medical literature to the regions of interest.

Figure 7:
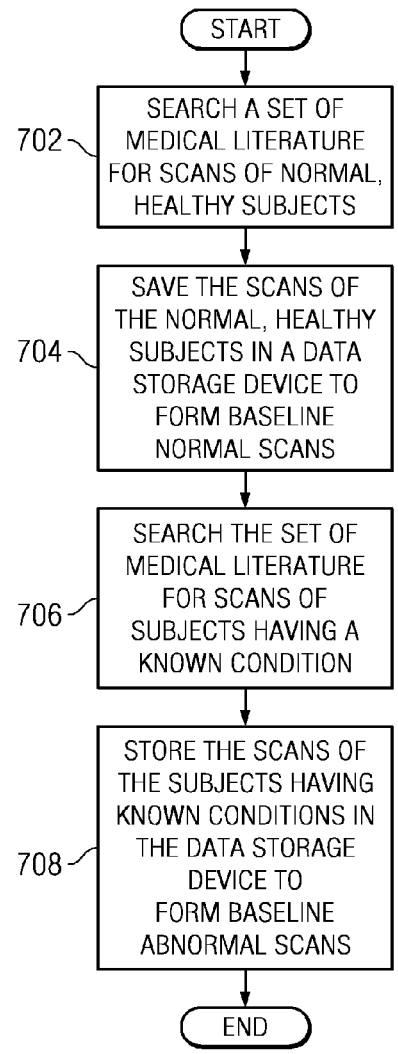
FIG. 7 is a flowchart illustrating a process for generating baseline control scans in accordance with an illustrative embodiment.

FIG. 7 is a flowchart illustrating a process for generating baseline control scans in accordance with an illustrative embodiment. The process in FIG. 7 may be implemented by software for generating a set of baseline control scans, such as medical data and text analytics 314 in FIG. 3.

The process begins by searching a set of medical literature sources for scans of normal, healthy subjects (step 702). The scans of the normal, healthy subjects are saved in a data storage device to form baseline normal scans (step 704). The process searches the set of medical literature sources for scans of subjects having known conditions (step 706). The conditions may be a disease, an illness, an infection, a deformity, or any other condition. The scans of the subjects having the known conditions are saved in the data storage device to form baseline abnormal scans (step 708) with the process terminating thereafter.

According to one embodiment of the present invention, a computer implemented method, apparatus, and computer program product for analyzing neurological images is provided. A neuroimage mapping manager compares a set of brain scans for a patient to a set of baseline control scans to automatically identify regions of interest in the set of patient scans. A region of interest is an area in a scan that shows an indication of a potential abnormality. The neuroimage mapping manager searches a set of electronic medical literature sources for medical literature relevant to the regions of interest in the set of patient scans to form relevant medical literature. The neuroimage mapping manager correlates portions of the relevant medical literature describing the regions of interest in the set of patient scans to the regions of interest in the set of patient scans to form correlated portions of the relevant medical literature. The neuroimage mapping manager then outputs the regions of interest in the set of patient scans and a set of links to the correlated portions of the relevant medical literature.

The neuroimage mapping manager automates the assessment of neuroimage data and literature to detect and document whether a disease process may be occurring or whether a condition may be present. The neuroimage mapping manager improves the speed and potentially the accuracy of diagnostic and treatment processes. The neuroimage mapping manager automates the determination of regions of interest in neuroimage data via mapping of literature into magnetic resonance imaging scans or positron emission tomography scans.

The neuroimage mapping manager lessens the workload on physicians and researchers, permits more accurate data interpretation and analysis of patient scans, and allows physicians and researchers to more quickly reach a diagnosis of neuropsychiatric conditions. In addition, the neuroimage mapping manager provides a decision support tool for clinicians in both clinical and research settings, to help them determine whether talk therapy, pharmacotherapy, or mechanical electroconvulsive therapy will be most effective by linking neuroimage data with the relevant medical literature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A method of analyzing neurological images, the method comprising:
    comparing, by a processor, a set of brain scans for a patient to a set of baseline control scans to automatically identify a set of regions of interest in the set of patient scans, wherein a region of interest is an area in a scan that shows an indication of a potential abnormality;
    searching, by the processor, a set of electronic medical literature sources for medical literature relevant to the set of regions of interest in the set of patient scans to form relevant medical literature;
    correlating, by the processor, portions of the relevant medical literature describing the set of regions of interest in the set of patient scans to the set of regions of interest in the set of patient scans to form correlated portions of the relevant medical literature;
    generating, by the processor, a result, wherein the result comprises the set of patient scans and a set of links to the correlated portions of the relevant medical literature;
    presenting, by the processor, the set of regions of interest to a user;
    responsive to receiving a selection of a set of additional regions of interest in the set of patient scans from the user to form a set of user selected regions of interest, adding, by the processor, the set of user selected regions of interest to the set of regions of interest in the set of patient scans; and responsive to receiving a selection of a set of undesired regions of interest in the set of patient scans from the user to form a set of de-selected regions of interest, removing, by the processor, the set of de-selected regions of interest from the set of regions of interest in the set of patient scans.

2. The method of claim 1 wherein portions of the relevant medical literature describing the set of regions of interest in the set of patient scans comprises a set of brain scans in the relevant medical literature showing areas of a brain having an identified abnormality that corresponds to the potential abnormality shown in the set of regions of interest in the set of patient scans.

3. The method of claim 1 wherein searching the set of electronic medical literature sources further comprising:

identifying, by the processor, the set of electronic medical literature sources; and searching, by the processor, medical literature available from the set of electronic medical literature sources using at least one of data mining, search engines, and queries to identify the relevant medical literature in the medical literature available from the set of electronic medical literature sources.

4. The method of claim 1 wherein the set of baseline control scans comprises a set of baseline normal scans, and further comprising:

receiving, by the processor, a set of brain scans for a set of healthy subjects in various demographic groups to form the baseline normal scans; and analyzing, by the processor, the baseline normal scans to identify a normal appearance of areas in normal brain scans, wherein a normal brain scan is a scan that does not show indications of disease or abnormalities in the areas in the normal brain scans.

5. The method of claim 1 wherein the set of baseline control scans comprises a set of baseline abnormal scans, and further comprising:

receiving, by the processor, a set of brain scans for a set of subjects in various demographic groups having identified abnormalities in the set of brain scans to form the baseline abnormal scans; and analyzing, by the processor, the baseline abnormal scans to identify an abnormal appearance of areas in brain scans, wherein an abnormal scan is a scan that shows indications of disease or abnormalities in the areas of the brain scans.

6. The method of claim 1 wherein the set of brain scans comprises a set of positron emission tomography scans of the patient.

7. The method of claim 1 wherein the set of brain scans comprises a set of magnetic resonance imaging scans of the patient.

8. The method of claim 1 wherein the set of links to the correlated portions of the relevant medical literature are embedded in the set of patient scans.

9. A computer program product for analyzing neurological images, the computer program product comprising:

a non-transitory computer usable medium having computer usable program code embodied therewith, the computer usable program code comprising:

computer usable program code configured to compare a set of brain scans for a patient to a set of baseline control scans to automatically identify a set of regions of interest in the set of patient scans, wherein a region of interest is an area in a scan that shows an indication of a potential abnormality;

computer usable program code configured to search a set of electronic medical literature sources for medical literature relevant to the set of regions of interest in the set of patient scans to form relevant medical literature;

computer usable program code configured to correlate portions of the relevant medical literature describing the set of regions of interest in the set of patient scans to the set of regions of interest in the set of patient scans to form correlated portions of the relevant medical literature;

computer usable program code configured to generate a result, wherein the result comprises the set of patient scans and a set of links to the correlated portions of the relevant medical literature;

computer usable program code configured to present the set of regions of interest to a user;

computer usable program code configured to add a set of user selected regions of interest to the set of regions of interest in the set of patient scans in response to receiving a selection of a set of additional regions of interest in the set of patient scans from the user to form the set of user selected regions of interest; and computer usable program code configured to remove a set of de-selected regions of interest from the set of regions of interest in the set of patient scans in response to receiving a selection of a set of undesired regions of interest in the set of patient scans from the user to form the set of de-selected regions of interest.

10. The computer program product of claim 9 wherein portions of the relevant medical literature describing the set of regions of interest in the set of patient scans comprises a set of brain scans in the relevant medical literature showing areas of a brain having an identified abnormality that corresponds to the potential abnormality shown in the set of regions of interest in the set of patient scans.

11. The computer program product of claim 9 wherein searching the set of electronic medical literature sources further comprising:

computer usable program code configured to identify the set of electronic medical literature sources; and computer usable program code configured to search medical literature available from the set of electronic medical literature sources using at least one of data mining, search engines, and queries to identify the relevant medical literature in the medical literature available from the set of electronic medical literature sources.

12. The computer program product of claim 9 wherein the set of baseline control scans comprises a set of baseline normal scans, and further comprising:

computer usable program code configured to receive a set of brain scans for a set of healthy subjects in various demographic groups to form the baseline normal scans; and computer usable program code configured to analyze the baseline normal scans to identify a normal appearance of areas in normal brain scans, wherein a normal brain scan is a scan that does not show indications of disease or abnormalities in the areas in the normal brain scans.

13. The computer program product of claim 9 wherein the set of baseline control scans comprises a set of baseline abnormal scans, and further comprising:

computer usable program code configured to receive a set of brain scans for a set of subjects in various demographic groups having identified abnormalities in the set of brain scans to form the baseline abnormal scans; and computer usable program code configured to analyze the baseline abnormal scans to identify an abnormal appearance of areas in brain scans, wherein an abnormal scan is a scan that shows indications of disease or abnormalities in the areas of the brain scans.

14. The computer program product of claim 9 wherein the set of brain scans comprises at least one of a set of positron emission tomography scans of the patient and a set of magnetic resonance imaging scans of the patient.

15. The computer program product of claim 9 wherein the set of links to the correlated portions of the relevant medical literature are embedded in the set of patient scans.

16. An apparatus comprising:
a bus system;
a communications system coupled to the bus system;
a non-transitory memory connected to the bus system, wherein the non-transitory memory includes computer usable program code; and
a processing unit coupled to the bus system, wherein the processing unit executes the computer usable program code to compare a set of brain scans for a patient to a set of baseline control scans to automatically identify a set of regions of interest in the set of patient scans, wherein a region of interest is an area in a scan that shows an indication of a potential abnormality; search a set of electronic medical literature sources for medical literature relevant to the set of regions of interest in the set of patient scans to form relevant medical literature; correlate portions of the relevant medical literature describing the set of regions of interest in the set of patient scans to the set of regions of interest in the set of patient scans to form correlated portions of the relevant medical literature; and generate a result, wherein the result comprises the set of patient scans and a set of links to the correlated portions of the relevant medical literature; present the set of regions of interest to a user; responsive to receiving a selection of a set of additional regions of interest in the set of patient scans from the user to form a set of user selected regions of interest, add the set of user selected regions of interest to the set of regions of interest in the set of patient scans; and responsive to receiving a selection of a set of undesired regions of interest in the set of patient scans from the user to form a set of de-selected regions of interest, remove the set of de-selected regions of interest from the set of regions of interest in the set of patient scans.

17. The apparatus of claim 16 wherein the processor unit further executes the computer usable program code to identify the set of electronic medical literature sources; and search medical literature available from the set of electronic medical literature sources using at least one of data mining, search engines, and queries to identify the relevant medical literature in the medical literature available from the set of electronic medical literature sources.

18. The apparatus of claim 16 wherein the processor unit further executes the computer usable program code to receive a set of brain scans for a set of subjects in various demographic groups having identified abnormalities in the set of brain scans to form the baseline abnormal scans; and analyze the baseline abnormal scans to identify an abnormal appearance of areas in brain scans, wherein an abnormal scan is a scan that shows indications of disease or abnormalities in the areas of the brain scans.

19. The apparatus of claim 16 wherein the processor unit further executes the computer usable program code to receive a set of brain scans for a set of healthy subjects in various demographic groups to form the baseline normal scans; and analyze the baseline normal scans to identify a normal appearance of areas in normal brain scans, wherein a normal brain scan is a scan that does not show indications of disease or abnormalities in the areas in the normal brain scans.

20. An apparatus for mapping medical literature onto neurological images, the apparatus comprising:
a non-transitory memory storing instructions for a neuroimage mapping manager and at least one processing unit for executing the instructions, wherein the neuroimage mapping manager performs an analysis on neurological images of a patient and automatically identifies a set of regions of interest and maps relevant portions of medical literature to the set of regions of interest, the neuroimage mapping manager further comprising:
a comparator, wherein the comparator compares a set of brain scans for a patient to a set of baseline control scans to automatically identify set of regions of interest in the set of patient scans, wherein a region of interest is an area in a scan that shows an indication of a potential abnormality;
a medical data and text analytics component, wherein the medical data and text analytics component searches a set of electronic medical literature sources for medical literature relevant to the set of regions of interest in the set of patient scans to form relevant medical literature, and wherein the medical data and text analytics component further comprises a correlation engine, wherein the correlation engine correlates portions of the relevant medical literature describing the set of regions of interest in the set of patient scans to the set of regions of interest in the set of patient scans to form correlated portions of the relevant medical literature; and
an input/output device, wherein the input/output device presents the set of regions of interest automatically selected by the neuroimage mapping manager to a user and prompts the user to indicate whether the user desires to select one or more additional regions of interest to be added to the set of regions of interest or select one or more undesired regions of interest to be removed from the set of regions of interest; and wherein the neuroimage mapping manager adds the one or more additional regions of interest to the set of regions of interest in the set of patient scans in response to the input/output device receiving a selection of at least one additional region of interest from the user, and wherein the neuroimage mapping manager removes de-selected regions of interest from the set of regions of interest in response to receiving a selection of a set of de-selected regions of interest to be removed from the set of regions of interest from the user, wherein the neuroimage mapping manager generates a result of the analysis of the neurological images, wherein the result comprises the set of regions of interest in the set of patient scans and a set of links to the correlated portions of the relevant medical literature.

21. The apparatus of claim 20 further comprising:
a set of computers, wherein the non-transitory memory storing instructions for the neuroimage mapping manager is located on the set of computers.

22. The apparatus of claim 20 wherein the medical data and text analytics analyzes baseline normal scans to identify a normal appearance of areas in normal brain scans in response to receiving a set of brain scans for a set of healthy subjects in various demographic groups to form the baseline normal scans and, wherein a normal brain scan is a scan that does not show indications of disease or abnormalities in the areas in the normal brain scans; and wherein the medical data and text analytics analyzes baseline abnormal scans to identify an abnormal appearance of areas in brain scans in response to receiving a set of brain scans for a set of subjects in various demographic groups having identified abnormalities in the set of brain scans to form the baseline abnormal scans, wherein an abnormal scan is a scan that shows indications of disease or abnormalities in the areas of the brain scans.

* * * * *